US008582712B2

(12) United States Patent
Karev et al.

(10) Patent No.: US 8,582,712 B2
(45) Date of Patent: Nov. 12, 2013

(54) METHODS OF DETECTION AND IDENTIFICATION OF CARBON- AND NITROGEN-CONTAINING MATERIALS

(75) Inventors: Alexander Ivanovich Karev, Moscow (RU); Valery Georgievich Raevsky, Moscow (RU); Leonid Zavenovich Dzhilavyan, Moscow (RU); Louis Joseph Brothers, Union, KY (US); Larry K. Wilhide, Newville, PA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 0 days.

(21) Appl. No.: 13/253,927

(22) Filed: Oct. 5, 2011

(65) Prior Publication Data
US 2012/0140863 A1    Jun. 7, 2012

Related U.S. Application Data

(60) Provisional application No. 61/534,177, filed on Sep. 13, 2011, provisional application No. 61/534,219, filed on Sep. 13, 2011.

(30) Foreign Application Priority Data

Dec. 6, 2010 (RU) .................................. 2010149620
Dec. 6, 2010 (RU) .................................. 2010149621

(51) Int. Cl.
*G21K 5/00*    (2006.01)
(52) U.S. Cl.
USPC .................. 376/157; 376/153; 250/269.1

(58) Field of Classification Search
USPC .................. 376/157, 153; 250/269.1
See application file for complete search history.

(56) References Cited

U.S. PATENT DOCUMENTS

| | | | | |
|---|---|---|---|---|
| 3,832,545 A | * | 8/1974 | Bartko ........................... | 376/159 |
| 4,756,866 A | * | 7/1988 | Alvarez ......................... | 376/157 |
| 4,980,901 A | * | 12/1990 | Miller ............................ | 378/45 |
| 5,115,459 A | * | 5/1992 | Bertozzi ........................ | 378/88 |
| 6,552,347 B1 | * | 4/2003 | Dimcovski ................. | 250/363.01 |
| 2002/0169351 A1 | * | 11/2002 | Brown .............................. | 588/1 |
| 2008/0156997 A1 | * | 7/2008 | Kearfott ..................... | 250/390.04 |

FOREIGN PATENT DOCUMENTS

| | | | |
|---|---|---|---|
| KR | 10-0261746 | | 1/2000 |
| KR | 100261746 | * | 1/2000 |
| RU | 2185614 | * | 7/2002 |
| RU | 2226686 | * | 4/2004 |

OTHER PUBLICATIONS

Tower, W.P., et al., "Imaging Carbon and Nitrogen Concentrations and the Interdiction of Concealed Narcotics and Explosives," Virginia Journal of Science 1993, 44; 293-300.*
Karev, A.I., et al., "The High Efficiency Complex for Detection of Landmines, Detection of Explosives and Landmines," 2002, 185-193.*

(Continued)

*Primary Examiner* — Jack W Keith
*Assistant Examiner* — Sean P Burke
(74) *Attorney, Agent, or Firm* — Steinfl & Bruno, LLP.

(57) ABSTRACT

Methods for detecting and identifying carbon- and/or nitrogen-containing materials are disclosed. The methods may comprise detection of photo-nuclear reaction products of nitrogen and carbon to detect and identify the carbon- and/or nitrogen-containing materials.

19 Claims, 3 Drawing Sheets (56) References Cited

OTHER PUBLICATIONS

Knapp, E.A., et al., "Direct Imaging of Explosives, Applied Radiation and Isotopes," 2000, 53: 711-716.*

Trower, W.P., et al., Imaging Carbon and Nitrogen Concentrations and the Interdiction of Concealed Narcotics and Explosives, Virginia Journal of Science 1993, 44: 293-300.

Karev, A.I., et al., The High Efficiency Complex for Detection of Landmines, Detection of Explosives and Landmines 2002, 185-193.

Knapp, E.A., et al., Direct Imaging of Explosives, Applied Radiation and Isotopes 2000, 53: 711-716.

PCT International Search Report mailed on May 14, 2012 for PCT Application No. PCT/US2011/054996 filed on Oct. 5, 2011 in the name of Lawrence Livermore National Security, LLC et al.

PCT Written Opinion mailed on May 14, 2012 for PCT Application No. PCT/US2011/054996 filed on Oct. 5, 2011 in the name of Lawrence Livermore National Security, LLC et al.

PCT International Search Report mailed on May 14, 2012 for PCT Application No. PCT/US2011/054998 filed on Oct. 5, 2011 in the name of Lawrence Livermore National Security, LLC et al.

PCT Written Opinion mailed on May 14, 2012 for PCT Application No. PCT/US2011/054998 filed on Oct. 5, 2011 in the name of Lawrence Livermore National Security, LLC et al.

* cited by examiner

METHODS OF DETECTION AND IDENTIFICATION OF CARBON- AND NITROGEN-CONTAINING MATERIALS

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

CROSS REFERENCE TO RELATED APPLICATIONS

The present application claims priority to Russian Application No. 2010149621, filed on Dec. 6, 2010, Russian Application No. 2010149620, filed on Dec. 6, 2010, U.S. Provisional Application 61/534,177, filed on Sep. 13, 2011, and U.S. Provisional Application 61/534,219, filed on Sep. 13, 2011, all of which are incorporated herein by reference in their entirety. The present application is also related to U.S. patent application Ser. No. 13/253,934, entitled "Device for Detection and Identification of Carbon- and Nitrogen-Containing Materials", and filed on even date herewith, the disclosure of which is attached hereto as Annex A.

FIELD

The present disclosure relates to methods for detection and identification of carbon- and nitrogen-containing materials. In particular, it relates to methods for detection and identification of carbon- and/or nitrogen-containing materials by photo-nuclear detection.

SUMMARY

According to a first aspect, a method for detecting carbon- and/or nitrogen-containing materials is provided, comprising irradiating a test object by a pulse of gamma radiation, the test object comprising carbon- and/or nitrogen-containing material; measuring of a secondary radiation from decay products of nitrogen-12 and boron-12 isotopes, wherein the nitrogen-12 and boron-12 isotopes are formed by the irradiation of the carbon- and/or nitrogen containing material from the test object; recording time spectra of signals from the secondary radiation; analyzing the spectra to determine if nitrogen-12 and/or boron-12 isotopes are present based on the decay signature thereof, thus detecting nitrogen- and/or carbon-containing materials.

According to a second aspect of the disclosure, a method for identifying carbon- and/or nitrogen-containing materials is provided, comprising: irradiating a test object by a pulse of gamma radiation, the test object comprising carbon- and/or nitrogen-containing material(s); measuring of a secondary radiation from decay products of nitrogen-12 and boron-12 isotopes, wherein the nitrogen-12 and boron-12 isotopes are formed by the irradiation of the carbon- and/or nitrogen containing material from the test object; recording time spectra of signals from the secondary radiation; analyzing the spectra to calculate a relative content of nitrogen to carbon of the test object based on the signals of nitrogen-12 and/or boron-12 isotopes; and identifying the carbon- and/or nitrogen-containing materials of the test object by comparison of the relative content of nitrogen to carbon to a database of similar information based on known samples.

Further embodiments of the present disclosure can be found in the written specification, drawings and claims of the present application. According to some embodiments of the present disclosure, the teachings of the present disclosure provide methods for detection and identification of carbon- and nitrogen-containing materials. In particular, it provides methods for detection and identification of carbon- and/or nitrogen-containing materials by photo-nuclear detection.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

The present disclosure relates to methods for detection and identification of carbon- and nitrogen-containing materials. In particular, it relates to methods for detection and identification of carbon- and nitrogen-containing materials by a photo-nuclear detection. The methods for detection and identification of carbon- and nitrogen-containing materials can be used for, as examples but not limited to, finding concealed explosive materials and/or narcotic substances as part of activities such as screening baggage of air passengers, screening cargo containers, screening vehicles such as trucks at border crossings, performing customs inspections, guard posts inspections, mail inspections, or clearing of landmines from areas within a framework of humanitarian activities, etc. The methods described in the present disclosure may be used in stationary or mobile installations.

The methods of the present disclosure describe an object to be tested that is irradiated by a pulse of primary gamma radiation. Upon irradiation, a time spectrum of secondary radiation from the object may be measured and recorded, a time delay of possibly several milliseconds may occur between termination of the irradiation and the measuring and recording of the secondary radiation time spectrum. The recording may last for a period of time possibly similar to half-lives of the isotopes of $^{12}B$ and $^{12}N$. A recorded time spectrum of signals may be transformed from differential to integral form. An analysis of two or more portions of the integral time spectrum may be used to calculate the relative content of nitrogen and carbon in the object. An aggregate set of calculated values for the relative concentrations of nitrogen and carbon of known substances of interest may be determined and stored. Comparison of a relative content of nitrogen and carbon in the irradiated object for the study may be compared to values in the aggregate set based on known substances of interest to detect and/or identify substances of interest in the irradiated object.

The methods may be further utilized to reduce false positives in a detection of one or more carbon- and nitrogen-containing materials, by identification of substances from a relative content of nitrogen and carbon in a tested material. The method may be applicable to increase reliability of detection, to increase accuracy of identification, to decrease likelihood of false positives, and/or to increase throughput of a detector of carbon- and nitrogen-containing materials.

The methods of the present disclosure relate to a technique of photonuclear detection of carbon- and nitrogen-containing materials as proposed in Reference [1] and developed in References [2-4]. This technique may be utilized for direct detection of carbon- and nitrogen-containing materials and comprises measuring decay products of short-lived isotopes Boron-12 ($^{12}$B) and Nitrogen-12 ($^{12}$N), having decay half-lives $T_{1/2} \cong 20.2$ and 11.0 milliseconds, respectively. These isotopes are formed from nuclei of $^{14}$N (the isotope content in the natural mixture $\eta \cong 99.63\%$) and $^{13}$C (the isotope content in the natural mixture $\eta \cong 1.107\%$) upon their irradiation by incident gamma quanta having energy $E_\gamma$ greater than the threshold value $E_{\gamma t}$, as a result of the following photonuclear reactions:

(1)

(2)

(3)

These reactions as markers may be utilized to enable a useful selectivity in the detection of materials containing nitrogen and/or carbon. Since irradiation of most chemical elements besides carbon and nitrogen by gamma pulses with $E_\gamma < \sim 55$ MeV will form practically no other isotopes having $T_{1/2} \approx (1-100)$ ms, these nuclear reactions may serve as markers for detecting and quantifying relative carbon to nitrogen content. The isotopes $^{12}$B and $^{12}$N are β-active, and in the process of decay emit electrons and positrons with maximal energies of ~13 MeV and ~17 MeV respectively, which, upon braking and decelerating within a substance, will emit secondary gamma quanta.

All secondary quanta, whether those produced by braking, de-excitation of those formed in the decays of the $^{12}$C nucleus, or annihilation of those emitted upon decays of $^{12}$N positrons, together with electrons and positrons, constitute secondary decay products and can be measured by a detector. Consequently, when an object to be tested is irradiated by a pulse of sufficiently powerful gamma radiation and a duration on the order of several microseconds, then in the following time interval up to ~100 ms, if the object contains a sufficient concentration of nitrogen and/or carbon, it will respond with a flux of secondary particles from the decay of the isotopes $^{12}$B and $^{12}$N. In the case where no carbon- or nitrogen-containing materials are present, there should be no such flux measured within the measured period of time within the energy range of interest.

Additional characteristics of radionuclides formed by the indicated irradiation of nitrogen and/or carbon as shown in Equations (1)-(3) worth noting include that both the initiating radiation and secondary radiation signals of interest are formed by fluxes of gamma radiation having a penetrating capability on the order of mm to tens of cm range in most materials. Thus the methods of detection of carbon- and/or nitrogen-containing materials as described in the present disclosure, using a photonuclear technique, can have sensitivity in depths of detection within concealed materials, which is supported by the results of computer modeling of such operation as shown in Reference [5].

The utilization of the photonuclear technique of the methods of the present disclosure can provide useful selectivity in the detection of carbon- and/or nitrogen-containing materials. In addition to signals from specific carbon- and/or nitrogen-containing materials of interest, it is also possible to detect background or extraneous signals from materials that are not of interest, but which do contain nitrogen and/or carbon. Suppression of false positives may be especially important some areas of utilization where speed of operation and accuracy are important and may be executed by a calculation of a nitrogen to carbon ratio for the tested object by the methods of the present disclosure with identifying precision.

A technique for identifying carbon- and nitrogen-containing materials has been previously presented with a prototype in Reference [4], based on analyzing the time distribution of signals from secondary radiation with a photonuclear technique of detection. The technique described in Reference [4] consists of the following: Upon a single irradiation of a test material containing nitrogen and/or carbon by a beam of gamma quanta with energy greater than 31 MeV, as a result of the reactions described in Equations (1)-(3), nuclei of short-lived isotopes $^{12}$B and $^{12}$N are formed. The relative concentration of these isotopes is uniquely dependent on the relative concentrations of nitrogen and carbon in the irradiated test material and determines a unique signature of the scanned substance. Upon radioactive decay, the isotopes of $^{12}$B and $^{12}$N form a flux of secondary radiation and the time-dependence of the flux of secondary radiation is determined by the half-life periods of the isotopes and initial relative concentrations of each isotope. A change in the number of radioactive nuclei of each particular isotope with time due to radioactive decay is described by Equation (4):

$$N(t) = N_0 \times \exp(-\lambda \times t) \quad (4)$$

where:
  $N(t)$ is the number of undecayed nuclei at the moment of time t;
  $N_0$ is the initial number of (generated) nuclei (at t=0); and
  $\lambda$ is the decay constant ($\lambda = \ln(2)/T_{1/2}$).

For the decay of the two isotopes of interest, the number of radioactive nuclei can be described by:

$$N(t) = N_{0(N-12)} \times \exp(-\lambda_{N-12} \times t) + N_{0(B-12)} \times \exp(-\lambda_{(B-12)} \times t) \quad (5)$$

at $t=0$:

$$N_{0\Sigma} = N_{0(B-12)} + N_{0(N-12)}; \quad (6)$$

where:
  $\lambda_{(N-12)}$ and $\lambda_{(B-12)}$ are the decay constants for $^{12}$N and $^{12}$B, respectively;
  $N_{0(N-12)}$ and $N_{0(B-12)}$ are the numbers of the (generated) nuclei of $^{12}$N and $^{12}$B; and
  $N_{0\Sigma}$ is the total number of (generated) nuclei of the radioactive isotopes $^{12}$B and $^{12}$N.

Based on the relationship shown in Equations (5) and (6), one may calculate an initial relative concentration of $^{12}$N and $^{12}$B isotopes and identify a scanned material by analyzing form and path of the time-dependence for the flux of secondary radiation from the decay of $^{12}$N and $^{12}$B. The form and path of the time-dependence (i.e. the shape of the curve) for the flux of secondary radiation may be measured as a time spectrum of secondary radiation from decays in an experiment after the end of the initial irradiation pulse.

The results from analysis of the time spectra of the decay products of the isotopes $^{12}$B and $^{12}$N can be represented in the form of the value of the parameter k, which is described by Equation (7):

$$k = k_{N-12} = 1 - k_{b-12}, \quad (7)$$

where: $k_{B-12} = N_{0(B-12)}/N_{0\Sigma}$, $k_{N-12} = N_{0(N-12)}/N_{0\Sigma}$.

Knowledge of the k values of known carbon- and/or nitrogen-containing materials may enable one to determine whether the irradiated test material belongs to the category of one or more known carbon- and/or nitrogen-containing materials of interest by comparing results obtained from operation of the detector with results obtained by irradiating standard known samples, thus enabling identification of the test material.

In the application of Equations (1)-(7) in the detection and identification of carbon- and/or nitrogen-containing materials described in Reference [4], the device measures a differential time spectrum, where in each measured time interval (also bin, step, or width of channel) a number of decays of the two isotopes of interest is measured (e.g. $n\{t\}=(dN/dt) \times \Delta t$) so that the time distribution of the events measured by the detector from decays of the isotopes $^{12}N$ and $^{12}B$ and measured in the process of operating the device, can be written by the expression:

$$n\{t\} = \lambda_{(N-12)} \times N_{0(N-12)} \times \exp(-\lambda_{(N-12)} \times t) \times \Delta t + \lambda_{(B-12)} \times N_{0(B-12)} \times \exp(-\lambda_{(B-12)} \times t) \times \Delta t, \quad (8)$$

where $\Delta t$ is the width of a channel (or time step) in the measured time distribution.

In practice, a certain complexity of processing the obtained signals may be due to an accumulating of signals for constructing a time distribution in a real detector for particular uses which may require a shorter interval of time for feasibility of operation and for avoidance of distorting signals. In the first several milliseconds after completion of the irradiation, the gamma detector may receive numerous gamma quanta connected primarily with the $(n,\gamma)$ reactions caused by photoneutrons, which can strongly distort the measurement results. Therefore, one may choose to conduct analysis of a portion of the time spectrum beginning after the end of an irradiation pulse followed by a certain delay to avoid confounding effects of such distorting signals.

On the other hand, the duration of collection can also be limited by, for example, specific applications which may require a certain rapidity of detector operation. Faster detection may be beneficial while scanning an object to be tested when it may be necessary to perform multiple irradiations of various zones in order to obtain a complete picture or a more reliable identification. At least due to the two identified limitations imposed on the time interval for compiling the decay curve, immediate measurement of the quantity $N_{0\Sigma}$ and direct calculation of the value of k may be prevented, thus lowering the overall productivity of the device, as well as the accuracy and reliability of the obtained results.

The problem stated in the previous paragraphs may be addressed at least by the methods of the present disclosure which may be utilized to increase the accuracy and reliability of operation of a photonuclear detector for the detection and identification of carbon- and/or nitrogen-containing materials. The detection and identification may also be applied for some applications with an increase in productivity.

The methods of the present disclosure may comprise the following steps: Conducting an irradiation of a tested object by a pulse of primary gamma radiation. Conducting registration of the time spectrum of the secondary radiation after a delay of approximately several milliseconds after irradiation ends and lasting for a period of time comparable to the half-life periods of the isotopes, $^{12}B$ and $^{12}N$, of interest. The time spectrum of signals, which may be recorded after the delay, may be subsequently transformed from a differential to an integral form. By analysis of two or more portions of the integral time spectrum, the values of k corresponding to these time intervals may be calculated. Further analysis of the calculated values of k may determine whether the irradiated material belongs to the category of nitrogen- or carbon-containing materials of interest.

The methods of the present disclosure may enable determination of the value of k, proceeding from two measured values of $n(t)$ corresponding to various moments of time t. In this case one may obtain a system of two equations, linear with respect to the desired $N_{0(N-12)}$ and $N_{0(B-12)}$:

$$\begin{cases} n\{t_i\} = \lambda_{(N-12)} \times N_{0(N-12)} \times \exp(-\lambda_{(N-12)} \times t_i) \times \Delta t + \lambda_{(B-12)} \times N_{0(B-12)} \times \exp(-\lambda_{(B-12)} \times t_i) \times \Delta t \\ n\{t_j\} = \lambda_{(N-12)} \times N_{0(N-12)} \times \exp(-\lambda_{(N-12)} \times t_j) \times \Delta t + \lambda_{(B-12)} \times N_{0(B-12)} \times \exp(-\lambda_{(B-12)} \times t_j) \times \Delta t \end{cases} \quad (9)$$

Solving the Equations Set (9) yields the values $N_{0(N-12)}$, $N_{0(B-12)}$, and $k = N_{0(N-12)}/(N_{0(N-12)} + N_{0(B-12)})$. Applying the described procedure to the aggregate of the values i and j=i+1, it is possible to obtain a sequence of values $k_i$ relating to each interval $\Delta t$ of the time spectrum.

Further, it is possible to convert from a differential form of describing the process of isotope decay to its integral description, and to work with a total number of events collected in several channels, corresponding to a time interval $(t_2-t_1)$. Such conversion may reduce statistical error in determining values of $N_{0(N-12)}$, $N_{0(B-12)}$, and consequently k, caused by a relatively small statistical error accumulated in each individual channel of a time distribution. For an integral description, the difference between the quantity of undecayed nuclei at the moments of time $t_1$ and $t_2$ may be described as:

$$N\{t_1\} - N\{t_2\} = N_{0(N-12)} \times [\exp(-\lambda_{(N-12)} \times t_1) - \exp(-\lambda_{(N-12)} \times t_2)] + N_{0(B-12)} \times [\exp(-\lambda_{(B-12)} \times t_1) - \exp(-\lambda_{(B-12)} \times t_2)] = \Sigma n_i, \quad (10)$$

where $\Sigma n_i$ is the sum of events measured in the channels corresponding to the time interval $(t_2-t_1)$. Thus, if one takes two intervals $(t_2-t_1)$ and $(t_4-t_3)$, then from the corresponding equations of the type in Equations Set (10), we obtain an Equations Set (11) analogous to the Equations Set (9) as follows:

$$\Sigma n_i = N_{0(N-12)} \times [\exp(-\lambda_{(N-12)} \times t_1) - \exp(-\lambda_{(N-12)} \times t_2)] + N_{0(B-12)} \times [\exp(-\lambda_{(B-12)} \times t_1) - \exp(-\lambda_{(B-12)} \times t_2)],$$

$$\Sigma n_j = N_{0(N-12)} \times [\exp(-\lambda_{(N-12)} \times t_3) - \exp(-\lambda_{(N-12)} \times t_4)] + N_{0(B-12)} \times [\exp(-\lambda_{(B-12)} \times t_3) - \exp(-\lambda_{(B-12)} \times t_4)] \quad (11)$$

where $\Sigma n_i$ and $\Sigma n_j$ are the sums of signals measured in the channels corresponding to the time intervals $(t_2-t_1)$ and $(t_4-t_3)$. Solving Equations Set (11) with respect to the values of $N_{0(N-12)}$ and $N_{0(B-12)}$ allows for the determination for the values of k.

With an appropriate selection of $t_1$, $t_2$, $t_3$, and $t_4$, an integral description may enable a calculation of the values of $N_{0(N-12)}$, $N_{0(B-12)}$, and a possible value of k that may be associated with the total number of events collected in all channels of the measured time spectrum with reasonable statistical accuracy in the performed measurements.

The integral description of the decay process may be useful to calculate, with reasonable accuracy, $k_i$ values which are associated with different time intervals. To obtain the integral description from the experimental time spectrum for a limited time interval one can, for example, do following steps: 1)

Calculate the $N_{0(N-12)}$ and $N_{0(B-12)}$ for two time intervals with large statistic by Equations (11); 2) Calculate the $N(t_1) = N_{0(N-12)} \times \exp(-\lambda_{(N-12)} \times t_1) + N_{0(B-12)} \times \exp(-\lambda_{(B-12)} \times t_1)$ (in accordance with Equation (5)), where $t_1$ is the time distance between the irradiation pulse and start of the collecting of the time spectrum; 3) Calculate the next value $N(t_i)$ as $N(t_{i+1}) = N(t_i) - \Delta n_{i+1}$, where $\Delta n_{i+1}$ is events in the (i+1) bin of the time spectrum. This integral distribution may enable a determination of the parameter k as the function k(t) which can be of statistical accuracy.

The above paragraphs describe a method according to an embodiment of the present disclosure, for generating a time series for k(t) at each measured point (t) which may be utilized for identifying the presence or absence of nitrogen and/or carbon in a given material. In an ideal case with the presence of nitrogen and/or carbon, the function k(t) should be a constant and independent from time; a plot of the function should be a line with slope of zero on a (k, t) coordinate space. Conversely, the line approximating the function k(t) should have a noticeable slope on the (k, t) coordinate space. This description can serve as an additional criterion for the reliability of the result. Furthermore, the possible value of k indicated above yields a value for photonuclear information from the material which characterizes the presence of nitrogen and/or carbon in the material, and their relative concentrations.

Thus, the methods of the present disclosure offer several additional operations and features not described in the prototype technique shown in Reference [4]. For example the methods of the present disclosure allow for an analysis of data obtained and measured by a photonuclear detector in real-life conditions, and introduces new criteria governing the reliability of detecting substances that contain nitrogen or carbon, such as:

1. A step can be included for conversion from depicting measured differential spectra to integral form, which can substantially increase statistical accuracy of the measurements.
2. A method is proposed for analyzing time spectra in a limited time interval. A limit from the direction of shorter times can diminish the influence on a time spectrum of background processes caused primarily by photoneutrons formed by interaction of the electron beam with individual parts of the device. A limit from the side of longer times may increase the overall operating speed of the detector.
3. A criterion is proposed for evaluation of reliability for the result, based on analysis of the time-dependence of the value of k, calculated for various intervals of time.

In another embodiment of the present disclosure and for verification of the methods of the present disclosure, computer modeling has been performed according to the method for detecting and identifying of carbon- and/or nitrogen-containing materials which may be concealed under a few cm of other materials.

A computer model is created which accounts for the processes that occur in an irradiated sample, as well as the output of secondary radiation and its registration by a secondary-radiation detector; the procedure for discovering and identifying carbon- and/or nitrogen-containing materials is thus modeled. A value is determined for the parameter $k_{true}$, equal to the ratio of nuclei of the isotope $^{12}N$ ($N_{0(N-12)}$) to the total number $N_{0\Sigma}$ of the nuclei of radionuclides formed in the process and a time spectrum is constructed of events measured by the detector. This spectrum is further processed with the aid of the above-described procedure, and a value $k_{meas}$ is determined corresponding to the selected time intervals.

The computer model of the method is executed with the following set conditions: The sample is irradiated for 6 microseconds (μs) with a beam of gamma quanta generated in a tungsten bremsstrahlung target having a thickness of 0.35 mm by an incident beam of electrons with energy of 55 MeV, a current of 30 mA, and a pulse length of 6 μs. A secondary-radiation detector with an area of 1 m² is placed at a distance of 60 cm from the sample, and the efficiency of the detector is set at 100%. The following materials are used as targets for the modeling: a 100-mg mass of trinitrotoluene (TNT) and a 100-mg mass of graphite; a background spectrum is also generated, adequate to load the detector with a background from nuclear reactions of the (n,γ) type caused by the photoneutrons. Below are shown the results obtained by modeling an irradiation of the target with one pulse of the accelerator.

Figure 1:
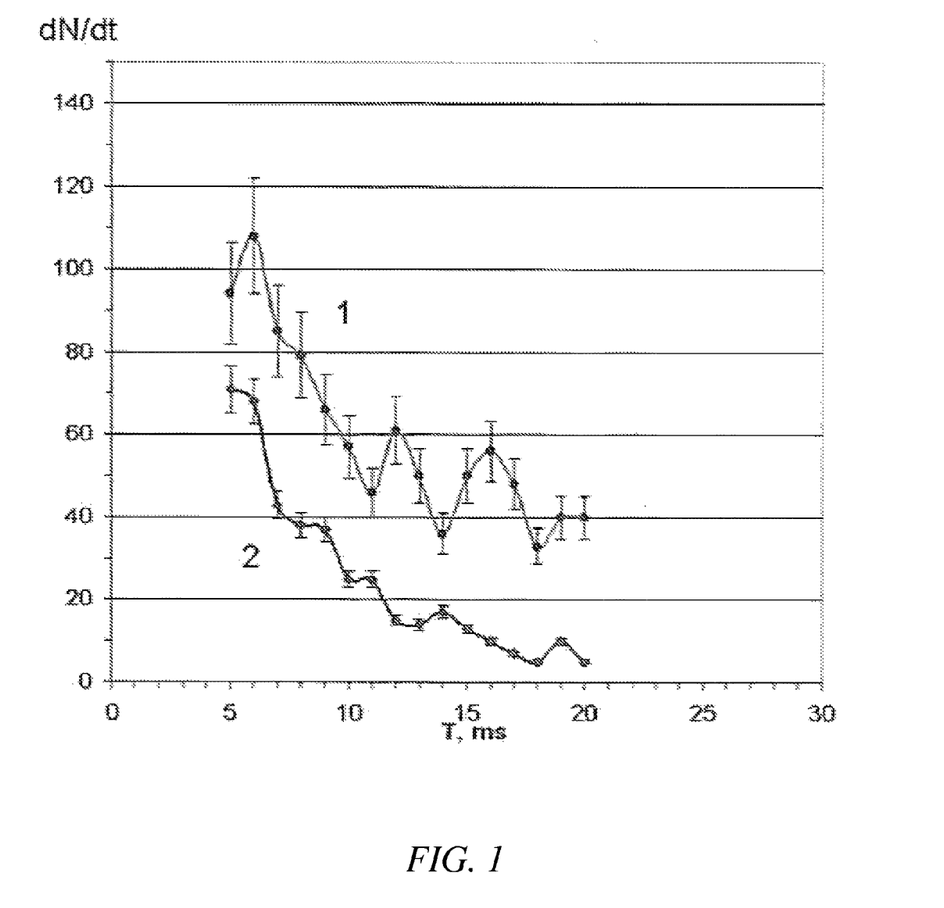
FIG. 1 shows two differential time spectra plots as measured by a detector based on a computer modeled embodiment of the method of the present disclosure.

FIG. 1 shows two differential time spectra plot as measured by the detector based on embodiments of the method of the present disclosure. The difference time spectrum is created by the computer model for the irradiation of a sample containing TNT (Curve 1) and a typical spectrum generated by the background processes (Curve 2), which is a computer simulation of real background data. Other set conditions for the computer model include that the secondary-radiation detector is switched on 5 ms after the end of the irradiation pulse, the recording of events takes place over an interval of 15 ms, and the width of a channel of the time analyzer is 1 ms. The error bars indicate a confidence range for each data point based the statistical range of one standard deviation for n runs of the simulation at each data point.

Figure 2:
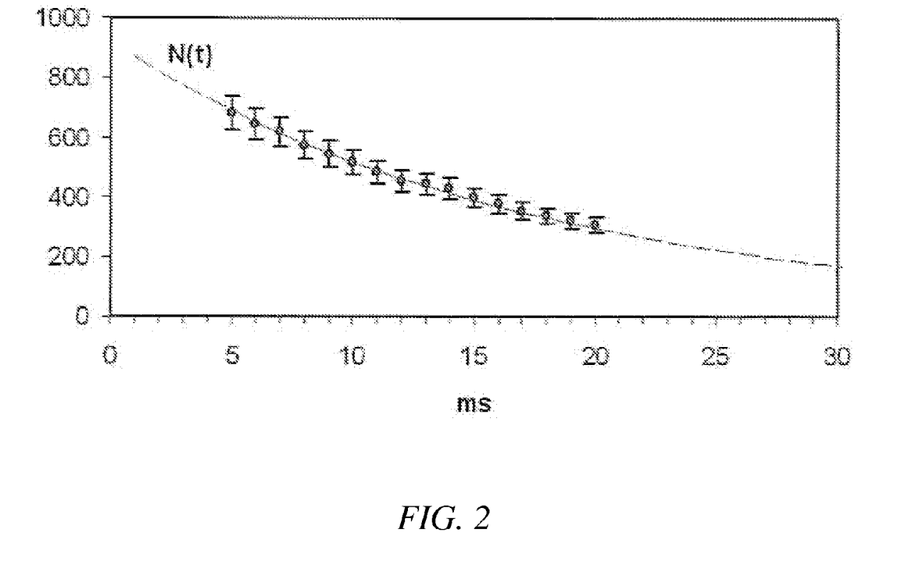
FIG. 2 shows an integral time spectrum N(t) plot of secondary radiation for trinitrotoluene (TNT), obtained from a differential time spectrum (Curve 1 of FIG. 1).

FIG. 2 shows an integral time spectrum N(t) plot of secondary radiation for TNT, obtained from the differential time spectrum (Curve 1 on FIG. 1), using a procedure, for example, as shown in paragraph [0028]. The time spectrum shown in FIG. 2 is a curve depicting the number of undecayed (remaining) nuclei of $^{12}N$ and $^{12}B$ in the irradiated substance plotted as a function of time as shown at each time step, $t_i$. The error bars in FIG. 2 also indicate the statistical accuracy of the data shown.

From a comparison of the corresponding curves in FIGS. 1 and 2, the error bars for the integral spectrum appear to be significantly smaller than the corresponding error range for the differential spectrum. The smaller error bars suggest that more accurately calculated values for $N_{0(N-12)}$, $N_{0(B-12)}$, and k, may be determined from the integral spectral data.

Thus, the methods of the present disclosure may be utilized to not only identify materials having similar elemental ratio of carbon to nitrogen, but also to exclude objects whose elemental content differs from known samples. For example, if the measured secondary radiation response as modeled by equation (11) shows a non-constant response of k versus time, this response may serve as a qualification marker indicating the presence of one or more additional radioactive isotope besides $^{12}N$ and $^{12}B$ in the irradiated material.

Figure 3:
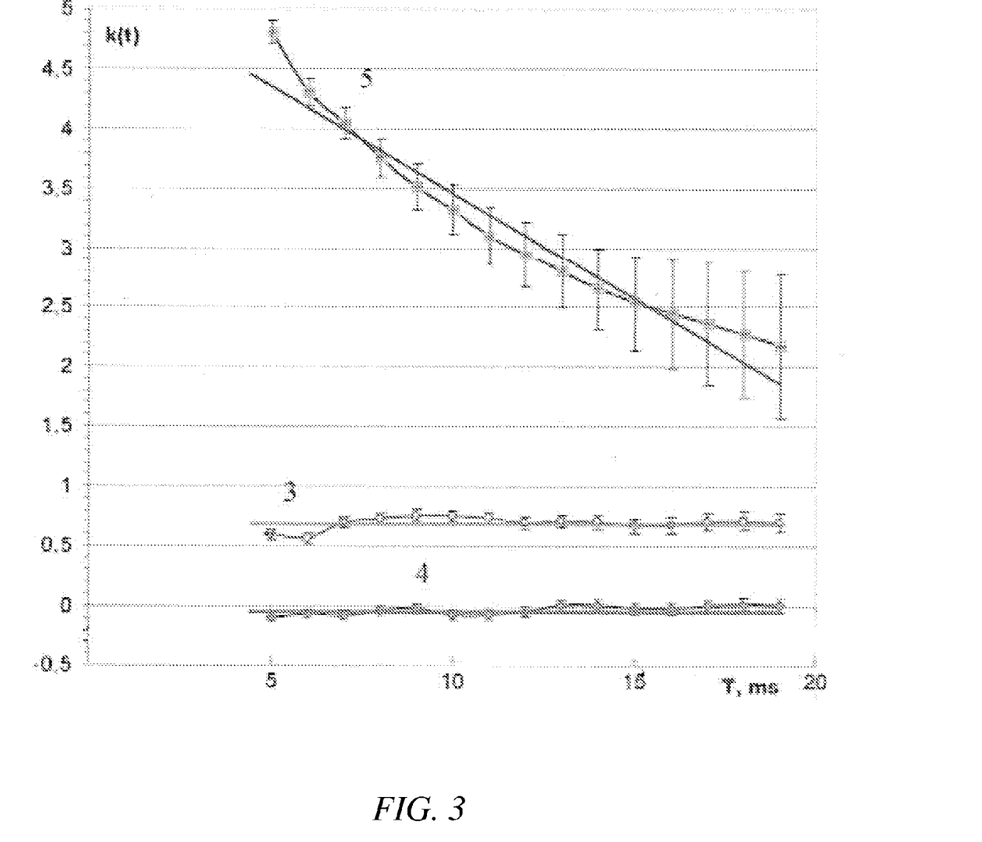
FIG. 3 shows a plot showing k, a ratio of nuclei of the isotope $^{12}N$ to the total number of the nuclei of radionuclides formed, for TNT (3), graphite (4), and a background process (5) as functions of time.

FIG. 3 shows a plot of k(t) for TNT (3), graphite (4), and the background process (5) as functions of time. The plot of the background process (5) shows a variation in time for an observed k, which may enable the identification of carbon and/or nitrogen containing materials in the object of interest. As an example of a non-unique determination of the parameter k with the aid of the proposed method, we may use the data presented in FIG. 3, showing the behaviors of k(t) for TNT (3), graphite (4), and the background process (5).

Table 1 shows the combined data from modeling processes of registration, where for various detected materials are shown the "true" values $k_{true}$ calculated from a known quantity of generated nuclei of radionuclides; measured values $k_{meas}$ obtained in the course of processing the time spectra by the proposed method; and slope as tangent of slope angle of the straight lines which approximate the k(t)-dependence.

TABLE 1

| Substance | $k_{true}$ | $k_{meas}$ | Tangent of slope angle of line approimating k(t) |
|---|---|---|---|
| TNT | 0.72 | 0.696 ± 0.062 | 0.003643 |
| Graphite | 0.0 | −0.04 ± 0.07 | 0.004143 |
| Background | — | 2.962 ± 0.062 | −0.173105 |

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually, even if the citation refers to only the first page of the reference.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. U.S. Pat. No. 4,756,866.
2. E. A. Knapp, A. W. Saunders, and W. P. Trower: Direct Imaging of Explosives. Proceedings of MINE'99 Euroconference on: Sensor systems and signal processing techniques applied to the detection of mines and unexploded ordnance, Oct. 1-3, 1999. Villa Agape, Firenze, Italy; Laboratorio Ultrasuoni e Controlli Non Distruttivi, Universita di Firenze, Italy. http://demining.jrc.it/aris/events/mine99/start.htm
3. A device for discovery of concealed explosive materials. Russian Federation Patent No. 2185614. BI (Bulletin of Inventions) No. 20, 2002.
4. A method and device for discovery and identification of concealed explosive materials and narcotic substances. Russian Federation Patent No. 2226686, 2004.
5. A. I. Karev, V. G. Raevsky, J. A. Konyaev, A. S. Rumyantsev, R. R. Iliutschenko: The High Efficiency Complex for Detection of Landmines. In: Proceedings of NATO Advanced Research Workshop #977941, "Detection of Explosives and Land Mines: Methods and Field Experience," St. Petersburg, Russia, 11-14 Sep. 2001, NATO-Science Series book, Kluwer Academic Publisher, Netherlands.

The invention claimed is:

1. A method for detecting carbon- and/or nitrogen-containing materials, comprising:
   irradiating a test object by a single pulse of gamma radiation, the test object comprising carbon- and/or nitrogen-containing material;
   measuring a secondary radiation from decay products of nitrogen-12 and boron-12 isotopes, wherein the nitrogen-12 and boron-12 isotopes are formed by the irradiation of the carbon- and/or nitrogen containing material from the test object;
   recording one or more time spectra of signals from the secondary radiation; and
   analyzing the time spectra to determine one or more parameters indicative of a number of nitrogen-12 or boron-12 isotopes with respect to a total number of nitrogen-12 isotopes and boron-12 isotopes,
   wherein the analyzing of the time-spectra to determine the one or more parameters is performed with data from two or more time intervals of recorded time spectra of signals from the secondary radiation of the test object.

2. The method according to claim 1, wherein the analyzing of the time spectra to determine the one or more parameters comprises using computer processing to identify whether said one or more parameters are known to be associated with a material of interest.

3. The method according to claim 1, wherein the recording of the time spectrum begins after the end of the irradiation pulse and a timed delay.

4. The method according to claim 1, wherein the recording of the one or more time spectra is for a time span based on decay half-lives of the nitrogen-12 and boron-12 isotopes.

5. The method according to claim 1, wherein the analyzing of the time spectra comprises transforming measured differential time spectra into integral time spectra.

6. A method for identifying carbon- and/or nitrogen-containing materials, comprising:
   irradiating a test object by a single pulse of gamma radiation, the test object comprising carbon- and/or nitrogen-containing material;
   measuring a secondary radiation from decay products of nitrogen-12 and boron-12 isotopes, wherein the nitrogen-12 and boron-12 isotopes are formed by the irradiation of the carbon- and/or nitrogen containing material from the test object;
   recording one or more time spectra of signals from the secondary radiation;
   analyzing the time spectra to calculate a relative content of nitrogen to carbon of the test object based on one or more parameters indicative of a number of nitrogen-12 or boron-12 isotopes with respect to a total number of nitrogen-12 isotopes and boron-12 isotopes; and
   identifying the carbon- and/or nitrogen-containing materials of the test object by comparing the one or more parameters to a database of similar information based on known samples to evaluate whether the one or more parameters are indicative of a material of interest,
   wherein the analyzing of the time spectra to calculate the relative content of nitrogen to carbon of the test object is performed with data from two or more time intervals of recorded time spectra of signals from the secondary radiation of the test object.

7. The method according to claim 6, wherein the recording of the time spectrum begins after the end of the irradiation pulse and a timed delay.

8. The method according to claim 6, wherein the recording of the one or more time spectra is for a time span based on the decay half-lives of the nitrogen-12 and boron-12 isotopes.

9. The method according to claim 6, wherein the analyzing of the time spectra comprises transforming measured differential time spectra into integral time spectra.

10. The method according to claim 1, the method comprising providing a device, the device comprising:
   an electron accelerator, comprising a race-track microtron with an operating energy of >50 MeV and configured to generate pulses of accelerated electron beam;
   a breaking target, comprising tantalum and configured to receive the pulses of accelerated electron beam and generating an incident gamma radiation to be directed at a test object; and
   a radiation detector, comprising a water-filled Cherenkov radiation counter and configured to detect and measure secondary gamma radiation from carbon and/or nitrogen materials undergoing radioactive decay following irradiation of the test object by the incident gamma radiation.

11. The method according to claim 10 wherein the water-filled Cherenkov radiation counter comprises:
   a tank filled with water configured to interact with the secondary gamma radiation to generate Cherenkov radiation;
   a plurality of photodetectors configured to measure the generated Cherenkov radiation in the tank filled with water; and
   control electronics comprising a starting generator and a time analyzer and configured to:
      initiate each of the electron accelerator pulses;
      terminate each of the electron accelerator pulses;
      time a controlled delay;
      initiate measurements by photodetectors of the radiation detector only after the controlled delay after termination of each of the electron accelerator pulses; and
      terminate measurements by the photodetectors before initiating the next electron accelerator pulse.

12. The method according to claim 1, the method comprising providing a device, the device comprising:
   an electron accelerator configured to generate pulses of one accelerated electron beam;
   a breaking target configured to receive the pulses of the accelerated electron beam and generating an incident gamma radiation to be directed at a test object; and
   a radiation detector configured to detect and measure secondary gamma radiation from carbon- and/or nitrogen-containing materials in the test object undergoing radioactive decay following irradiation of the test object by the incident gamma radiation, thus detecting and identifying the carbon- and/or nitrogen-containing materials in the test object.

13. The method according to claim 12, wherein the device is adapted for detecting secondary gamma radiation from carbon and/or nitrogen containing materials in a test object concealed by one or more layers of concealment materials.

14. The method according to claim 13, the device further comprising control electronics, associated with the electron accelerator and the radiation detector, configured to:
   initiate each of the electron accelerator pulses;
   terminate each of the electron accelerator pulses;
   time a controlled delay;
   initiate measurements by photodetectors of the radiation detector only after the controlled delay after termination of each of the electron accelerator pulses; and
   terminate measurements by the photodetectors before initiating the next electron accelerator pulse.

15. The method according to claim 10 further comprising identifying the carbon- and/or nitrogen-containing materials of the test object by comparing the one or more parameters to a database of similar information based on known samples to evaluate whether the one or more parameters are indicative of a material of interest.

16. The method according to claim 6, wherein the material of interest is a hazardous substance in the test object.

17. The method according to claim 15, wherein the material of interest is a hazardous substance in the test object.

18. The method according to claim 1, wherein the one or more parameters are each defined as a ratio of the number of nitrogen-12 isotopes over the total number of nitrogen-12 and boron-12 isotopes.

19. The method according to claim 6, wherein the one or more parameters are each defined as a ratio of the number of nitrogen-12 isotopes over the total number of nitrogen-12 and boron-12 isotopes.

* * * * *